(12) United States Patent
Pompeo et al.

(10) Patent No.: US 9,072,294 B2
(45) Date of Patent: Jul. 7, 2015

(54) EMULSIFIER SYSTEM AND PESTICIDAL FORMULATIONS CONTAINING THE EMULSIFIER SYSTEM

(75) Inventors: Michael P. Pompeo, Sumter, SC (US); Alefesh Hailu, Cincinnati, OH (US)

(73) Assignee: Cognis IP Management GmbH, Duesseldorf (DE)

(*) Notice: Subject to any disclaimer, the term of this patent is extended or adjusted under 35 U.S.C. 154(b) by 680 days.

(21) Appl. No.: 11/600,991

(22) Filed: Nov. 17, 2006

(65) Prior Publication Data

US 2007/0191230 A1    Aug. 16, 2007

Related U.S. Application Data

(60) Provisional application No. 60/773,580, filed on Feb. 15, 2006.

(51) Int. Cl.
  *A01N 25/00* (2006.01)
  *A01N 25/30* (2006.01)
  *A61K 9/16* (2006.01)
  *A01N 25/04* (2006.01)
  *A01N 25/02* (2006.01)

(52) U.S. Cl.
  CPC .............. *A01N 25/30* (2013.01); *A61K 9/1629* (2013.01); *A01N 25/04* (2013.01); *A01N 25/02* (2013.01)

(58) Field of Classification Search
  CPC ............................. A01N 25/04; A61K 9/1629
  USPC .................................................. 424/405, 497
  See application file for complete search history.

(56) References Cited

U.S. PATENT DOCUMENTS

| | | | | |
|---|---|---|---|---|
| 2,861,108 A * | 11/1958 | Ballun et al. | ................... | 568/608 |
| 4,195,083 A * | 3/1980 | Hoy et al. | ..................... | 514/86 |
| 4,450,001 A | 5/1984 | Kaneko et al. | | |
| 4,840,942 A * | 6/1989 | Iwasaki et al. | ................. | 514/120 |
| 4,931,086 A * | 6/1990 | Moucharafieh | ............... | 504/112 |
| 4,938,797 A | 7/1990 | Hässlin et al. | | |
| 5,084,087 A * | 1/1992 | Hazen et al. | ................... | 504/364 |
| 5,466,659 A | 11/1995 | Keeney et al. | | |
| 5,500,219 A * | 3/1996 | Utz et al. | ....................... | 424/409 |
| 5,538,662 A | 7/1996 | Klier et al. | | |
| 5,558,806 A | 9/1996 | Policello et al. | | |
| 5,834,006 A | 11/1998 | Smith et al. | | |
| 5,905,072 A | 5/1999 | Capuzzi et al. | | |
| 5,916,967 A | 6/1999 | Jones et al. | | |
| 6,017,559 A | 1/2000 | Mulqueen et al. | | |
| 6,143,830 A * | 11/2000 | Utz et al. | ....................... | 525/240 |
| 6,165,939 A * | 12/2000 | Agbaje et al. | ................. | 504/105 |
| 6,432,884 B1* | 8/2002 | Lachut | ........................... | 504/363 |
| 6,566,308 B1* | 5/2003 | Aven | ............................. | 504/347 |
| 6,586,366 B1 | 7/2003 | Auda et al. | | |
| 6,586,479 B2 | 7/2003 | Miller et al. | | |
| 2002/0160916 A1 | 10/2002 | Volgas et al. | | |
| 2002/0168422 A1* | 11/2002 | Hei et al. | ...................... | 424/661 |
| 2004/0063513 A1 | 4/2004 | Zen | | |
| 2004/0071653 A1 | 4/2004 | Bratescu et al. | | |
| 2005/0124738 A1 | 6/2005 | Sivik et al. | | |
| 2006/0183642 A1* | 8/2006 | Otsubo et al. | ................. | 504/344 |

FOREIGN PATENT DOCUMENTS

| | | |
|---|---|---|
| AU | 2004100006 A4 | 3/2004 |
| CN | 1449660 A * | 10/2003 |
| EP | 0356812 | 3/1990 |
| WO | WO-98/12921 | 4/1998 |
| WO | WO-2006/050141 | 5/2006 |
| WO | WO-2006/052228 | 5/2006 |
| WO | WO-2006/098156 | 9/2006 |
| WO | WO-2007/030885 | 3/2007 |

OTHER PUBLICATIONS

Curtis M. Elsik, et al., "Microemulsion Formulation of Agricultural Adjuvants", Proceedings of 6th International Symposium on Adjuvants for Agrochemicals, ISAA 2001, Amsterdam, The Netherlands, Editor: Hans de Ruiter, Aug. 13-17, 2001, pp. 403-408.
TERGITOL™ XDLW Surfactant Technical Data Sheet.
GARLON® 4 Herbicide Material Safety Data Sheet.
GARLON® 4 Specialty Herbicide Specimen Label.
EP Supplementary Search Report in EP 07 75 0491, dated Aug. 17, 2012, 4 pgs.

* cited by examiner

*Primary Examiner* — Ali Soroush
(74) *Attorney, Agent, or Firm* — Servilla Whitney LLC

(57) ABSTRACT

The invention is an emulsifier adjuvant system for forming a substantially solventless or solvent free emulsifiable pesticidal composition. The emulsifier system comprises from about 25 to about 80% by weight, of surfactants in the emulsifier system, of at least one anionic surfactant having an average HLB value of from about 6 to about 11; and from about 20 to about 75% by weight of surfactants in the emulsifier system of at least one nonionic surfactant having an average HLB value of from about 11 to about 18.

The emulsifier and adjuvant system of the invention can form emulsifier concentrates of solventless pesticidal compositions with a concentration of the pesticidal composition up to about 90% by weight.

22 Claims, No Drawings

EMULSIFIER SYSTEM AND PESTICIDAL FORMULATIONS CONTAINING THE EMULSIFIER SYSTEM

CROSS REFERENCE TO RELATED APPLICATIONS

This application claims priority, under 35 U.S.C. §119(e), of U.S. Provisional Patent Application No. 60/773,580, filed on Feb. 15, 2006, the entire contents of which are incorporated herein by reference.

FIELD OF THE INVENTION

The invention relates to an emulsifying system and adjuvant for formulating water soluble or water emulsifiable pesticide formulations.

BACKGROUND OF THE INVENTION

Pesticide formulations are generally applied as dilute solutions or dispersions to the locus of the pest to be controlled. The dilute solution or dispersion is generally prepared in the field by dilution of a concentrate with water. The pesticide is then applied as a solution in water or an emulsion. The pesticide can also be applied as an emulsion of a solution in an organic solvent. However, due to environmental concerns, pesticidal formulations are preferably applied as a solution or a dispersion of the pesticide or a pesticide solvent mixture in water.

Adjuvants which improve the performance of the pesticide are generally added to the pesticide composition. This is applicable to both water soluble and water dispersible pesticidal formulations. The adjuvants are generally incorporated into pesticide formulations to improve their performance, increase their efficacy and reduce the amount of the pesticide which must be applied. The adjuvants take many forms but can be surfactant materials which potentiate or increase the activity of the pesticide. It is not certain how the potentiation or increase in activity occurs but it is believed that the adjuvant materials improve the contacting and absorption of the pesticide by the pest being treated.

Organic solvents particularly petroleum based solvents have become notorious in environmental circles and are believed to have an adverse effect on the health of persons in the vicinity in which the pesticide is being applied.

It would be an advantage if a pesticide could be formulated as a solventless or substantially solventless formulation which could be diluted in water or dispersed in water directly without the requirement for a solvent or a carrier.

BRIEF DESCRIPTION OF THE SEVERAL VIEWS OF THE DRAWINGS

Not applicable.

BRIEF DESCRIPTION OF THE INVENTION

Applicants have unexpectedly discovered an emulsifier and adjuvant system which can be utilized to formulate organic solvent free or substantially organic solvent free pesticide formulations.

The emulsifier and adjuvant system for a pesticidal formulation comprises:

(a) from about 20 to about 80% by weight, of surfactants in the emulsifier composition, of a hydrophobic anionic surfactant which is preferably oil soluble or mixtures containing at least one hydrophobic anionic surfactant having an average HLB of from about 6 to about 11 preferably comprising an alkali metal, alkaline earth metal, ammonium, amine or alkanol amine salt of an alkylbenzene sulfonate containing from about 8 to about 22 carbon atoms in the alkyl group; and (b) from about 20 to about 80% by weight, of surfactants in the emulsifier composition, of at least one hydrophilic nonionic surfactant or mixture of nonionic surfactants which are preferably hydrophilic having an average HLB of from about 11 to about 18 and preferably comprising a capped or uncapped ethylene oxide and/or propylene oxide copolymer which can be a statistical or block copolymer and preferably a block copolymer. Single nonionic surfactants and mixtures of nonionic surfactants have been found useful.

The emulsifier and adjuvant composition of the invention can contain additional anionic surfactants and additional nonionic surfactants. Preferably, the additional nonionic surfactants comprise aliphatic groups, cycloaliphatic groups and aromatic groups which have been alkoxylated, preferably alkoxylated with a nonblock mixture of ethylene oxide and propylene oxide, ethylene oxide alone or propylene oxide alone. The additional nonionic surfactants can also contain small amounts of butylene oxide groups.

As used herein, the term substantially solventless refers to a pesticidal composition containing up to about 10% by weight preferably up to 5% by weight of an organic solvent or carrier. Water and lower alcohol hydrotropes are not considered as solvents in the present invention. The solvents can be petroleum based, plant or animal based or synthetic materials. Preferably, the solvents comprise low molecular weight alcohol esters of fatty acids containing from about 8 to about 22 carbon atoms. The low molecular weight alcohols contain from 1 to about 4 carbon atoms. The fatty acid esters can be saturated or unsaturated, linear or branched. The small amount of solvent may be required in special cases to lower the viscosity of the pesticide so that it can be readily mixed with the emulsifier adjuvant composition and readily dispersed or dissolved in water. A solventless pesticidal formulation would contain no added solvents other than those which may accompany the pesticide due to its method of manufacture or to place it in the form of a liquid.

The pesticides which are useful in the practice of the present invention are liquid materials or low melting point solids which do not adversely interact or react with the emulsifier adjuvant composition. The pesticides can comprise mixtures of pesticides.

DETAILED DESCRIPTION OF THE INVENTION

The anionic surfactant preferably comprises an anionic surfactant or mixture of anionic surfactants having an average HLB value of from about 6 to about 11. More preferably the anionic surfactant comprises an alkali metal, an alkaline earth metal, ammonium, amine, alkanolamine salt of an alkylbenzene sulfonate. Preferably, the alkylbenzene sulfonate comprises an alkyl group containing from about 8 to about 22 carbon atoms. Preferably, the anionic surfactant comprises a calcium or magnesium salt of an alkylbenzene sulfonate and most preferably the calcium salt. The most preferred alkylbenzene sulfonate is the calcium salt of dodecylbenzene sulfonate.

The anionic surfactant portion of the emulsifier adjuvant composition may solely be the alkylbenzene sulfonate salt or can comprise a mixture of the alkylbenzene sulfonate salt with other anionic surfactants or the alkylbenzene sulfonate may be entirely absent from the composition. Preferably, the anionic surfactant comprises a mixture of anionic surfactants containing at least about 35% by weight preferably at least 40% by weight and most preferably at least 50% by weight of the alkylbenzene sulfonate salt (based on active components). The anionic surfactant comprises from 20% to 80% and preferably from 30% to 75% and most preferably from 35% to 70% by weight of the emulsifer adjuvant composition (based on active components).

The other anionic surfactants can comprise materials such as phosphate esters, alkyl sulfonates, alkyl sulfates, amphoteric surfactants such as the betaines, taurines and the like. Preferably the anionic surfactant or mixture of anionic surfactants is hydrophobic or oil soluble and has an average HLB value of from about 6 to about 11 and preferably from about 7.0 to about 10.

The anionic surfactant portion of the emulsifier adjuvant composition is preferably oil soluble.

The nonionic surfactants comprise an ethylene oxide-propylene oxide copolymer which may be capped or started at least at one end with an aliphatic, aromatic, cycloaliphatic aromatic aliphatic or aliphatic aromatic moiety. Preferably, an ethylene oxide-propylene oxide block copolymer is started with an aryl or aliphatic group which can be cyclic.

The nonionic surfactant copolymers can be random or block copolymers containing residues of ethylene oxide (EO), propylene oxide (PO) and butylene oxide (BO) in a ratio of from about (PO+BO):(EO) of from about 3:1 to 1:3 and preferably from about 2.5:1 to about 0.5:1 and most preferably from about 2:1 to about 1:1. The copolymers can contain up to about 150 alkoxide residues and most preferably up to about 100 alkoxide residues.

The additional nonionic surfactants can contain residues of a single alkoxide in an amount of from about 5 to about 100 residues.

The nonionic surfactant portion of the emulsifier adjuvant composition preferably has an average HLB value in the range of about 11 to about 18 and more preferably 11-16 and most preferably 11-13. The HLB value of the nonionic surfactant is an average of the HLB values of all of the nonionic surfactants. The HLB values of the nonionic surfactants are calculated using the Atlas Method $$\left\{HLB = \frac{20 \times 44 \times \text{moles } EO}{44 \times \text{moles } EO + \text{mol. weight of starting alcohol}}\right\}.$$

The nonionic surfactants are present in the system in a range of 80% to 20% by weight of the emulsifier adjuvant system preferably 70% to 25% and most preferably 65% to 30% by weight of the emulsifier adjuvant system (based on the active components).

The nonionic surfactants may additionally contain other nonionic surfactants which are not block copolymers of ethylene oxide and propylene oxide or the surfactant need not be alkoxylated. The nonionic surfactants can comprise random copolymers capped with aliphatic, aromatic, aromatic aliphatic or aliphatic aromatic groups. The nonionic surfactants can also comprise surfactants such as sorbitan esters which may be alkoxylated, polyglycosides which are known surfactants comprising an alkyl group containing from about 8 to about 20 carbon atoms and the like. The polyglycosides are acetals which are formed by the reaction of an alcohol with a sugar moiety. Commercially, alkylglycosides having from about 6 to about 20 carbon atoms in the alkyl group and a polyglucose residue having an average degree of polymerization of from about 1.1 to about 2 are well known in the art and are commercially available. The alkylglycosides can be further esterified, alkoxylated and the like. The average HLB value of the nonionic surfactant mixture is preferably in the range of from about 11 to about 16.

The nonionic surfactant or surfactant mixture is hydrophilic, preferably water soluble or water dispersible.

The advantage of the surfactant system of the invention is that it can be utilized to prepare pesticide concentrates which are substantially solvent free or solvent free. The pesticide can be formulated in concentrates which can contain up to about 90% preferably up to about 88% and most preferably up to about 86% by weight of the pesticide and can be readily emulsified when mixed with water. Preferably a formulation containing from about 90% to about 75% by weight and most preferably from 88% to 80% of the pesticide can be prepared. Compositions containing less than 80% of the pesticide can be prepared and the additional emulsifier can provide additional beneficial properties to the formulation. If the pesticide is water soluble, the surfactant system of the invention acts as an adjuvant and improves the efficacy of the pesticide when applied to control the pests. The pesticide must be compatible with the surfactant system, must not react to form inactive materials and the surfactant system must be soluble in the pesticide. If the pesticide contains an oil or oil like carrier, the concentration of the emulsifier composition in the formulation is based on the weight of pesticide and carrier.

If the pesticide is a water soluble material, the surfactant system of the present invention acts as an adjuvant since its emulsifying properties are not required unless an additional oil-like material is present in the mixture. As an adjuvant it generally improves the efficacy of the pesticide so that lower rates of application or more rapid action can be obtained, improves wetting and penetration of the pesticide.

The emulsifying system of the present invention is advantageous in that pesticidal formulations having an extremely high content of the pesticide can be formulated and readily dispersed in water at the point of use. The high concentration of the pesticides and the improved efficacy permits the formulation of concentrates with a high proportion of pesticide which reduces the shipping costs based on the active ingredients and reduces the amount of pesticide which is applied. The concentrates do not require substantial amounts of solvents and can be readily dispersed in an aqueous system.

However, if required, the emulsifier and adjuvant system of the invention can be introduced into mixture of pesticides with solvents to produce stable concentrates which form stable emulsion; however, the pesticide concentrates will contain lower concentrations of pesticides but will retain its improved properties.

The pesticides are preferably liquid materials or low melting solids and after mixing with the surfactant system of the invention are pourable concentrate formulations which are readily dispersible in water.

The surfactant system of the present invention is obtained by mixing the surfactants, preferably with mild heating to reduce the viscosity, then mixing the surfactant mixture and pesticide at an elevated temperature. Temperatures in the range of about 40 to about 80° C. are generally satisfactory for forming the blend of the surfactants and the technical pesticide concentrate.

The surfactant blend or the individual surfactants which form the blend can be introduced into the pesticide and mixed therewith. Preferably, each surfactant system or the individual surfactants are introduced into the pesticide at an elevated temperature. The elevated temperature generally forms a system with a reduced viscosity which enables the surfactant system to be mixed with the pesticide without the undue difficulty of mixing a high viscosity system.

If the viscosity of the emulsifier system or pesticide formulation is high, a small amount of a solvent can be introduced into the system to provide a readily mixable composition. The solvents can be the petroleum oils generally utilized in formulating pesticidal compositions. However, it is preferred that the solvent be an ester of a fatty acid with a monohydric alcohol of from about 1 to about 4 carbon atoms and preferably a methyl or ethyl ester. The fatty acid esters which can be utilized as a solvent in the composition of the invention generally have a low viscosity and a low freeze point. However, it is preferred that no organic solvent be present in the composition and preferably not more than about 5% by weight of solvent based on the mixture of the surfactant mixture and the pesticide. It has been unexpectedly discovered that the surfactant system of the present invention can be utilized to form pesticidal compositions which are readily emulsifiable without the use of solvents and particularly petroleum derived solvents.

The pesticidal compositions which are useful with the emulsifiable system of the present invention are liquids or low melting solids (30-40° C.) which are not adversely affected by the emulsifier system or do not react with the emulsifier system. The following is a listing of examples of pesticidal materials which can be used with the emulsifier system of the present invention. The listing is exemplary and there are many additional pesticides with which the emulsifier system of the invention is useful. The emulsifier and adjuvant system of the invention can be used with any pesticide which is liquid or low melting point solid and does not have an adverse reaction with the emulsifier system.

Useful pesticides include insecticides such as Malathion, Chlorpyrifos, Cypermethrin and Chloropicrin, herbicides such as Trifluralin, 2,4-D Ester, MCPA Isooctylester, Metolachlor, Acetochlor, Triclopyr and Roundup®, and fungicides such as Mefenoxam and Etridiazole.

The pesticidal composition according to the invention is prepared by mixing the emulsifier system or the individual emulsifiers with the pesticidal composition. The mixing can be carried out at room temperature or preferably at an elevated temperature to reduce the viscosity of the mixture.

The emulsifier system of the present invention can be mixed with the pesticidal material in a continuous or batch method. Static mixers, in-line mixers and the like are suitable. However, the emulsifier system can be mixed with the pesticidal composition in a batch mixer by merely heating and stirring or by circulation of the materials by an external pump arrangement. In the field, the pesticide concentrate can be added to water and stirred to form the pesticide at its application concentration.

Several emulsifier systems were prepared by mixing the surfactants by stirring at a temperature in the range of 40-70° C. After the mixture of the surfactants became homogenous, the surfactants were tested by adding the surfactants to a liquid pesticidal material at a slightly elevated temperature with mixing. The water emulsifiability of the pesticidal compositions containing the surfactant system of the invention was then tested according to the test method which follows. The test evaluates emulsion stability for emulsifiable oil-based concentrates. The procedure is applicable to any emulsifiable concentrate which gives rise, on dilution with water, to oil-in-water emulsions.

The method comprises mixing one milliliter of the emulsifiable concentrate with a standard water to give 100 ML of aqueous emulsion. The stability of the emulsion is then assessed in terms of the amount of free "oil or cream" which separates while the emulsion is allowed to stand undisturbed for a specific time. The ability of the system to re-emulsify at the end of a 24 hour time period is also determined.

The method for determining the emulsifiability of the concentrate of the invention is carried out as follows:

The test is carried out in a 100 ml. sedimentation glass stoppered measuring cylinder which is clean and free from grease. The cylinder is filled to 99 ml. with a standard water and one milliliter of the pesticide formulation is gently poured on the surface of the water in the cylinder and the stopper replaced. The stoppered cylinder is inverted ten times during a period of 20 seconds. The stoppered cylinder is permitted to stand for a period of time and the amount of oil which separates is determined by a light which is shined through the emulsion or reflected off the surface. The tube is permitted to remain undisturbed for a period of at least 30 minutes and the amount of free oil, froth, "cream" or solid matter present at the end of the time period is recorded. The glass cylinder is then permitted to stand for 24 hours and a second reading taken.

After 24 hours, the cylinder is then re-inverted 10 times and allowed to remain undisturbed for a further period of 30 min. The volume, if any, of free oil, froth, 'cream' or solid matter present at the end of the 30 min. period is then recorded.

The emulsifiability of the concentrates was determined utilizing standard waters. The standard waters were prepared as follows:

CIPAC MT 18.1 Standard Water B) 20 ppm $CaCO_3$ equivalent water

Transfer 40 ml. of CIPAC Standard Water C) 500 ppm $CaCO_3$ equivalent water was transferred into a 1,000 ml. volumetric flask. To the flask was added 0.168 grams of sodium hydrogencarbonate. The volumetric flask was filled to the volume with distilled/reverse osmosis water. The pH was adjusted if necessary to a range of 8-9 by the addition of hydrochloric acid or sodium hydroxide.

CIPAC MT 18.1 Standard Water C (500 ppm $CaCO_3$ equivalent water)

Dissolve 0.44 grams anhydrous calcium chloride and 0.203 grams of magnesium chloride hexahydrate in one liter of distilled/reverse osmosis water. Make up to a volume of 1,000 ml. Adjust the pH as necessary with hydrochloric acid/sodium hydroxide to a pH of 7.0-8.0.

CIPAC MT 18.1 Standard Water D (342 ppm $CaCO_3$ equivalent water)

Dissolve 0.304 grams anhydrous calcium chloride and 0.139 grams of magnesium chloride hexahydrate per liter of distilled/reverse osmosis water. Make up to the appropriate volume. Adjust the pH if necessary with hydrochloric acid/sodium hydroxide to a pH of 6.0-7.0.

$CaCO_3$ equivalent water (1026 ppm)

Dissolve 0.911 grams anhydrous calcium chloride and 0.416 grams of magnesium chloride hexahydrate per liter of distilled/reverse osmosis water and dilute to a one liter volume.

Emulsifiers

The following is a list of emulsifiers used in the examples to form the emulsifying adjuvant system of the present invention.

Agnique® ABS 60C—Dodecylbenzene Sulfonate Calcium Salt, HLB value 7-8 (60% active)

Agnique® STO-20—Sorbitan Trioleate EO (20), HLB value 11.1

Agnique® BP 24-36 $C_{12-14}$ PO(6) EO(3) block copolymer, HLB value 10-11

Tergitol® XD Butanol PO(31) EO(31) block copolymer, HLB value 12

Agnique® BP 4-3103 Butanol block copolymer with a block of random EO(31.2) PO(2.8) and a block of random PO(24.7) and EO(2.8) based on n-butanol. HLB value 11-14

Agnique® PE TDA-6—a mixed phosphate ester comprising a mixture of 40% by weight monoester and 60% by weight diester of tridecyl alcohol ethoxylated with 6 moles of ethylene oxide, and the free acid neutralized, HLB value 11-13

Agnique® BP NP-1530—Nonylphenol block copolymer PO(30) EO(15), HLB value 12-15

Agnique® PEG 400 MO (PEG monooleate), HLB value 11.8

Solvents

Agnique® ME 181U—Methyl oleate solvent
Edenor ME C12-18-C12-18 Methyl ester solvent The following emulsifier systems were prepared and their utility for emulsifying water insoluble pesticides was determined. The emulsifier systems were prepared by mixing the various surfactants at a temperature in the range of 40° C.-70° C. until the mixture became clear.

An amount of the surfactant systems of Examples 1 through 12 (shown in Table 1) were added to a heated technical pesticide and the mixture was stirred until the mixture of the surfactant system and the pesticide was clear. The emulsifiability of the composition was tested and the emulsion formed by adding the mixture to water was determined by the method described above. The results of the experiments are shown in Table 2.

Varying amounts of the emulsifier system of the invention are required to be added to the pesticidal formulations to achieve a formulation which is stable and can be diluted with water to form a stable emulsion.

As can be seen from the examples (2, 7, 9), the emulsifier adjuvant system of the present invention can also be useful in providing stable concentrate of pesticidal formulations containing solvents, particularly fatty acid ester solvents.

The emulsifier adjuvant system of the invention provide herbicidal performance equivalent or better than solvent-based concentrates in field trials.

TABLE 1

EMULSIFIER SYSTEM (Parts by weight)

| | Surfactant | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Agnique ® ABS 60C (60% Active) | 70 | 58 | 60 | 55 | 48.46 | 48.46 | 27.7 | 62.5 | 33.3 | 36.2 | 43 | 35 |
| Agnique ® BPNP-1530 | 42 | | | | | | | 33.5 | | | | |
| Agnique ® BP 24-36 | 28 | 37 | | | | | 16.9 | | | 20 | 12 | |
| Agnique ® BP 4-3103 | | 35 | | | 25.77 | 26.5 | 16.7 | | 20.1 | 21.9 | 22.5 | 37 |
| Agnique ® PE TDA-6 | | 35 | | | 25.77 | 26.5 | 16.7 | | 20.1 | 21.9 | 22.5 | 10 |
| Agnique ® ME 181U | | 15 | | | | | | | | | | |
| Tergitol ® XD | | | 40 | 25 | | | | | | | | |
| Agnique ® STO 20 | | | | 20 | | | | | | | | |
| Edenor ME ® C12-18 | | | | | | | 22.2 | | 26.5 | | | |
| Agnique ® PEG 400 MO | | | | | | | | | | | 12 | 10 |

The surfactant systems were evaluated on the following basis.

No separation at end of settling time period—Excellent
Trace separation at end of settling time period—Good
Trace to 0.5% separation at end of settling time period—Acceptable
More than 0.5% separation at end of settling time period—Not acceptable

TABLE 2

| Pesticide | Surfactant System | Surfactant System Percent by wgt. | Settling Time Period Hours Initial | Reemulsified after 24 hrs. | Ratio of Water Hardness 34 ppm | Water Hardness 342 ppm | Water Hardness 1000 ppm |
|---|---|---|---|---|---|---|---|
| Triclopyr* | 1 | 14 | 2 | | Good | Good | Good |
| Triclopyr* | 1 | 14 | | 0.5 | Excellent | Good | Acceptable |
| Triclopyr* | 2 | 18 | 0.5 | — | | Good | — |
| Triclopyr* | 2 | 18 | | 0.5 | — | Good | — |

TABLE 2-continued

| Pesticide | Surfactant System | Surfactant System Percent by wgt. | Settling Time Period Hours Initial | Reemulsified after 24 hrs. | Ratio of Water Hardness 34 ppm | Water Hardness 342 ppm | Water Hardness 1000 ppm |
|---|---|---|---|---|---|---|---|
| Triclopyr* | 3 | 14 | 2 | | Good | Good | Good |
| Triclopyr* | 3 | 14 | | 0.5 | Good | Good | Good |
| Triclopyr* | 4 | 14 | 0.5 | | Good | Good | Good |
| Triclopyr* | 4 | 14 | | 0.5 | Good | Good | Good |
| Triclopyr* | 5 | 14 | 2.0 | | Not Acceptable | Acceptable | Acceptable |
| Triclopyr* | 5 | 14 | | 0.5 | Acceptable | Acceptable | Acceptable |
| Triclopyr* | 5 | 20 | 2 | | Good | Good | Good |
| Triclopyr* | 5 | 20 | | 0.5 | Excellent | Excellent | Excellent |
| Triclopyr* | 6 | 14 | 2 | | Acceptable | Acceptable | Acceptable |
| Triclopyr* | 6 | 18 | 2 | | Good | Good | Good |
| Triclopyr* | 6 | 18 | | 0.5 | Excellent | Excellent | Excellent |
| Triclopyr* | 7 | 14 | 2 | | Acceptable | — | Acceptable |
| Triclopyr* | 8 | 14 | 2 | | Unacceptable | Acceptable | Acceptable |
| Triclopyr* | 8 | 14 | | 0.5 | Acceptable | Acceptable | Acceptable |
| Triclopyr* | 9 | 18 | 2 | | — | Excellent | — |
| Triclopyr* | 10 | 14 | 2 | | — | Good | — |
| Triclopyr* | 11 | 14 | 2 | | Not Acceptable | Not Acceptable | Acceptable |
| Triclopyr* | 11 | | | 0.5 | Not Acceptable | Acceptable | Acceptable |
| Triclopyr* | 11 | 20 | 2 | | Good | Good | Good |
| Triclopyr* | 11 | 20 | | 0.5 | Good | Excellent | Good |
| Triclopyr* | 12 | 10 | 1 | | Not Acceptable | — | — |
| Triclopyr* | 12 | 20 | 2 | | Good | Good | Acceptable |
| Triclopyr* | 12 | 20 | | 0.5 | Excellent | Excellent | Excellent |
| Technical Malathion | 3 | 14 | 2 | | Acceptable | Acceptable | Acceptable |
| Technical Malathion | 3 | | | 0.5 | Acceptable | Acceptable | Acceptable |
| Technical Malathion | 4 | 14 | 2 | | Good | Good | Acceptable |
| Technical Malathion | 4 | | | 0.5 | Excellent | Good | Good |
| Technical Metolachlor | 3 | 14 | 2 | | Excellent | Excellent | Good |
| Technical Metolachlor | 3 | 14 | | 0.5 | Excellent | Excellent | Acceptable |
| Technical Metolachlor | 4 | 14 | 2 | | Unacceptable | Unacceptable | Unacceptable |
| Technical Metolachlor | 4 | 14 | | 0.5 | Unacceptable | Unacceptable | Unacceptable |
| Technical Metolachlor | 4 | 20 | 1 | | Acceptable | Good | Excellent |
| Technical Metolachlor | 4 | 20 | | 0.5 | Good | Good | Excellent |

*Technical Triclopyr Butoxyethyl Ester

The above emulsifiers were tested at an emulsifier system level in a range of 14% to 20% by weight of the total of emulsifier system, pesticides and solvent, if present.

As can be seen from Table 2, not all emulsifier systems can satisfactorily emulsify all pesticide at a level of 14% by weight or less of the emulsifier system based on the weight of the formulation. However, the emulsifier system of the invention can satisfactorily emulsify many pesticide at concentration in the range of 12% to 20% by weight and preferably 10% to 20% by weight of the formulation.

Individual pesticides and mixtures of two or more pesticides can be prepared in a substantially solvent free form to provide a concentrate which can be readily added to water in the field and an emulsion formed with a minimum of mixing. The emulsions are generally stable for the period of at least about 24 hours.

What is claimed is:

1. An emulsifier and adjuvant system for a pesticidal formulation, the emulsifier and adjuvant system comprising:
    (a) from about 25% to about 80% by weight, based on the surfactants in the emulsifier system, of one or more hydrophobic anionic surfactants; and
    (b) from about 20% to about 75% by weight, based on the surfactants in the emulsifier system, of one or more hydrophilic random or block copolymer nonionic surfactants wherein the random or block copolymer comprises ethylene oxide (EO), propylene oxide (PO), and butylene oxide in a ratio of (PO+BO):(EO) of about 3:1 to 1:1;

wherein said one or more hydrophobic anionic surfactants and said one or more hydrophilic random or block copolymer nonionic surfactants are of the type and are present in the amounts effective to form a pesticide concentrate substantially free of petroleum derived solvents and having from about 75% by weight to about 95% by weight of a pesticide or mixture of pesticides, comprising a herbicide and/or fungicide, and wherein said pesticides are liquids or low melting solids in which said surfactants are soluble, thereby forming a liquid solution concentrate.

2. The emulsifier and adjuvant system of claim 1 further comprising one or more additional nonionic surfactants.

3. The emulsifier and adjuvant system of claim 1 further comprising one or more additional anionic surfacants.

4. The emulsifier and adjuvant system of claim 1 wherein the anionic surfactant comprises a salt of an alkylbenzene sulfonate containing from about 8 to 22 carbon atoms in the alkyl group.

5. The emulsifier and adjuvant system of claim 4 wherein the anionic surfactant comprises the calcium salt of dodecylbenzene sulfonate.

6. The emulsifier and adjuvant system of claim 2 wherein said additional nonionic surfactants comprise one or more members selected from the group consisting of ethoxylated-propoxylated surfactants, ethoxylated surfactants and propoxylated surfactants, which are nonblock capped at least at one end.

7. The emulsifier and adjuvant system of claim 1 wherein said one or more anionic surfactants has an average HLB value of about 6 to about 11.

8. The emulsifier and adjuvant system of claim 1 wherein said one or more nonionic surfactants has an average HLB value of about 11 to about 18.

9. A pesticidal liquid solution concentrate comprising a pesticide or mixture of pesticides, wherein the pesticide or mixture of pesticides comprises a herbicide and/or fungicide which is liquid or low melting, and the emulsifier and adjuvant system of claim 1, wherein the concentrate is substantially free of petroleum derived solvents.

10. The pesticidal liquid solution concentrate of claim 9 containing from about 10% to about 25% by weight of the emulsifier and adjuvant system, based on the total weight of the pesticidal concentrate.

11. The emulsifier and adjuvant system of claim 1 containing from 30% to 75% by weight of the anionic surfactant; and from 70% to 25% by weight of the nonionic surfactant.

12. The pesticidal liquid solution concentrate of claim 9 wherein said pesticide comprises a water-immiscible herbicide and/or fungicide.

13. The pesticidal liquid solution concentrate of claim 9 wherein said pesticide comprises a water-miscible herbicide and/or fungicide.

14. A liquid pesticidal composition comprising the liquid solution concentrate of claim 9 and from 95% to 99.999% by weight of water based on the total weight of the composition.

15. The emulsifier and adjuvant system of claim 1 containing from 35% to 70% by weight of the anionic surfactant and from 65% to 30% by weight of the non-ionic surfactant.

16. The pesticidal liquid solution concentrate of claim 9 containing from about 75% by weight to about 95% by weight of pesticide.

17. The pesticidal liquid solution concentrate of claim 9 containing from about 80% by weight to about 88% by weight of pesticide.

18. An emulsifier and adjuvant system for a pesticidal formulation, the emulsifier and adjuvant system consisting essentially of:
  (a) from about 25% to about 80% by weight, based on the surfactants in the emulsifier system, of one or more hydrophobic anionic surfactants;
  (b) from about 20% to about 75% by weight, based on the surfactants in the emulsifier system, of one or more hydrophilic random or block copolymer nonionic surfactants, wherein the random or block copolymer comprises ethylene oxide (EO), propylene oxide (PO), and butylene oxide in a ratio of (PO+BO):(EO) of about 3:1 to 1:1; and
  (c) optionally, an ester of a fatty acid with a monohydric alcohol of from 1 to 4 carbon atoms;

wherein said one or more hydrophobic anionic surfactants and said one or more hydrophilic random or block copolymer nonionic surfactants are of the type, and are present in the amounts effective to form a pesticide concentrate substantially free of petroleum derived solvents and having from about 75% by weight to about 95% by weight of a pesticide or mixture of pesticides, and wherein said pesticides are liquids or low melting solids in which said surfactants are soluble, thereby forming a liquid solution concentrate.

19. The emulsifier and adjuvant system of claim 18, wherein said pesticide or mixture of pesticides is selected from the group consisting of herbicides, fungicides and mixtures thereof.

20. The emulsifier and adjuvant system of claim 1, containing at most up to about 5% by weight of organic solvent or carrier.

21. The pesticidal liquid solution concentrate of claim 9, further comprising an ester of a fatty acid with a monohydric alcohol of from about 1 to about 4 carbon atoms.

22. The pesticidal liquid solution concentrate of claim 21, wherein the ester of a fatty acid with a monohydric alcohol is a methyl or ethyl ester.

* * * * *